(12) United States Patent
Kim

(10) Patent No.: US 12,102,551 B2
(45) Date of Patent: Oct. 1, 2024

(54) FINGER SPLINT FOR MANUAL THERAPY

(71) Applicant: Min Ki Kim, Seoul (KR)

(72) Inventor: Min Ki Kim, Seoul (KR)

(73) Assignee: Min Ki Kim, Seoul (KR)

( * ) Notice: Subject to any disclaimer, the term of this patent is extended or adjusted under 35 U.S.C. 154(b) by 0 days.

(21) Appl. No.: 18/555,645

(22) PCT Filed: Apr. 13, 2022

(86) PCT No.: PCT/KR2022/005355
§ 371 (c)(1),
(2) Date: Oct. 16, 2023

(87) PCT Pub. No.: WO2022/225252
PCT Pub. Date: Oct. 27, 2022

(65) Prior Publication Data
US 2024/0082041 A1 Mar. 14, 2024

(30) Foreign Application Priority Data
Apr. 22, 2021 (KR) ........................ 10-2021-0052358

(51) Int. Cl.
*A61F 5/058* (2006.01)
*A61L 15/12* (2006.01)
*A61L 15/14* (2006.01)

(52) U.S. Cl.
CPC ........ *A61F 5/05875* (2013.01); *A61L 15/125* (2013.01); *A61L 15/14* (2013.01)

(58) Field of Classification Search
CPC .... A61F 5/05875; A61F 5/0118; A61F 5/013; A61F 5/10; A61F 13/105; A61F 5/05866; A61F 5/00; A61F 5/01; A61F 5/0102; A61F 5/019; A61F 5/04; A61F 5/05; A61F 5/058; A61F 5/05841; A61F 5/05858; A41D 13/087
(Continued)

(56) References Cited

U.S. PATENT DOCUMENTS 1,773,108 A * 8/1930 Lichty ....................... A61F 5/50
128/880
2,740,121 A * 4/1956 Robert .................. A61F 13/105
2/21
(Continued)

FOREIGN PATENT DOCUMENTS

KR 10-2286026 B1 8/2021
WO WO 2017/091824 A1 6/2017

*Primary Examiner* — Keri J Nelson
*Assistant Examiner* — Seth R. Brown
(74) *Attorney, Agent, or Firm* — NSIP Law

(57) ABSTRACT

A finger splint for manual therapy according to the present invention comprises: a base sheet made of a metal material and of a certain length and width to surround a finger; a base hole formed through the center of the base sheet in a rhombus shape; a first hole extending through both upper left and right sides of the base hole along a portion of a periphery of the finger; and a second hole extending through both lower left and right sides of the base hole along the periphery of the finger to correspond to the position and size of the first hole. The finger splint for manual therapy according to the present invention has the effect of providing an excellent and comfortable fit on the basis of an ergonomic structure as well as sufficiently ensuring a basic fixing force.

9 Claims, 6 Drawing Sheets

(58) Field of Classification Search
USPC .................................... 602/22, 30; 128/880
See application file for complete search history.

(56) References Cited

U.S. PATENT DOCUMENTS

| | | | |
|---|---|---|---|
| 4,270,528 A | 6/1981 | Hanson | |
| 4,932,396 A | 6/1990 | Garris | |
| 10,383,763 B1* | 8/2019 | Leon | A61F 13/105 |
| 2004/0241215 A1* | 12/2004 | Lipman | A61F 13/0246 |
| | | | 424/445 |
| 2007/0207186 A1* | 9/2007 | Scanlon | A61F 2/91 |
| | | | 623/1.42 |
| 2012/0289877 A1 | 11/2012 | Hegland | |
| 2018/0368491 A1* | 12/2018 | Anunike | A63B 71/14 |
| 2021/0030595 A1* | 2/2021 | Liu | A61F 13/01046 |
| 2021/0260240 A1* | 8/2021 | Yoon | C08L 23/08 |

\* cited by examiner

FINGER SPLINT FOR MANUAL THERAPY

CROSS REFERENCE TO RELATED APPLICATIONS

This application is a U.S. National Stage Application of International Application No. PCT/KR2022/005355, filed on Apr. 13, 2022, which claims the benefit under 35 USC 119(a) and 365(b) of Korean Patent Application No. 10-2021-0052358, filed on Apr. 22, 2021, in the Korean Intellectual Property Office, the entire disclosure of which is incorporated herein by reference for all purposes.

TECHNICAL FIELD

The present disclosure relates to a finger splint for manual therapy and, more particularly, to a finger splint configured to obtain fixing force for a finger in the case of manual therapy and having an ergonomic structure by which excellent wearing sensation is provided and the finger is allowed to move to a predetermined degree so as to prevent uncomfortableness.

BACKGROUND ART

Manual therapy or manipulative therapy is a clinical practice mainly performed by physical therapists and oriental doctors with bare hands in order to treat musculoskeletal pain and disorders, and refers to a treatment of applying physical force to muscles, bones, and the like.

Such manual therapy mainly includes tension and relaxation of muscles, joint mobilization, and joint manipulation, and is mainly performed by experts. In general, manual treatment is performed by physical therapists, chiropractic is performed by chiropractors and oriental doctors, and massage is performed by massagers.

Manual therapy for joints, in particular, finger joints, is performed on patients who use their hands excessively or have finger numbness, fractures, ligament damage, carpal tunnel syndrome, etc. Manual therapy combines finger stretching and exercises by means of a separate protector surrounding the finger. At this time, the protector is called a splint, and the splint used on the finger is called a finger splint.

Such a finger splint is structured to surround a finger having a disease or the like. Unlike known bands or bandages, the finger splint serves to treat the disease while allowing the finger to move to a certain degree.

For such a finger splint (or finger guard), there are a number of prior art technologies. For example, a finger guard disclosed in Korean Registered Utility Model No. 476538 includes: a plurality of metal blocks; a fixing unit connecting the plurality of metal blocks; a body part formed by connecting the plurality of metal blocks using the fixing unit; and a tightening unit coupled to the metal block disposed on sides of the body part to form finger insertion portions on both sides of the body part and configured to tighten the body part. Each of the metal blocks has connecting rings on both sides in the transverse direction. Each of the connecting rings has an insertion portion extending therethrough to allow the fixing unit to be inserted into the insertion portion. The fixing unit includes a spring and a super-elastic iron core provided inside the spring. As the super-elastic iron core is inserted into the insertion portions of the connecting rings, the plurality of metal blocks are coupled to both sides of the fixing unit. The finger guard also includes an anti-release cap coupled to top and bottom ends of the fixing unit to prevent the metal blocks from being released. The finger guard is disclosed as providing a function able to safely protect a finger when a knife is used.

However, this prior art technology is specialized for protecting a finger from a knife, and thus there is a problem in that a function of controlling the range of motion or the movement of the finger in the case of manual therapy is not provided.

Therefore, there is a need to develop a novel and advanced finger splint which is specialized for manual therapy and, on the basis of an ergonomic design, can fix a finger while allowing the finger to move in a certain range when worn on the finger.

DISCLOSURE

Technical Problem

Accordingly, the present disclosure has been made in consideration of the above-described problems occurring in the above-described technology, and a major objective of the present disclosure is to provide a finger splint having a plurality of holes based on ergonomics in order to fix a finger for manual therapy while allowing the finger to move in an appropriate range.

Another objective of the present disclosure is to allow a finger to move in a predetermined range and enhance the degree of fixing of the finger by improving the cooperating structure of a base hole and first and second holes.

Another objective of the present disclosure is to enhance the finger fixing function by attaching a separate fixing band to the finger splint.

Another objective of the present disclosure is to reduce foreign body sensation and ensure excellent wearing sensation by stacking a functional layer on the rear surface of a base sheet made of a metal material.

Technical Solution

In order to realize at least one of the above-described objectives, a finger splint for manual therapy according to the present disclosure may include: a base sheet including a metal material and having a predetermined length and width to surround a finger; a diamond-shaped base hole provided in a central portion of the base sheet; a first hole extending along the circumference of a portion of the finger to connect portions adjacent to right and left upper portions of the base hole; and a second hole extending along the circumference of the finger to connect portions adjacent to right and left lower portions of the base hole, with the position and size of the second hole corresponding to the position and size of the first hole.

In addition, the finger splint may include a fixing band including an adhesive layer on a rear surface thereof and stacked on portions between ends of the first hole and between ends of the second hole.

In addition, each of the first and second holes may have an elliptical shape with the major axis thereof being in the circumferential direction of the finger.

Advantageous Effects

The finger splint for manual therapy according to the present disclosure provides the following effects:

1) The finger splint may obtain a sufficient amount of force for fixing a finger in the case of manual therapy and have an ergonomic structure by which excellent and comfortable wearing sensation is provided.

2) The finger splint may reliably allow the finger to move in a predetermined degree in order to minimize the uncomfortableness of a wearer.

3) The finger splint may allow the finger to move and prevent an increase in the fatigue of the finger or cracks in the finger splint when the finger is moved.

4) The finger splint may prevent the skin from unnecessary foreign body sensation and being hurt.

BEST MODE

Figure 1:
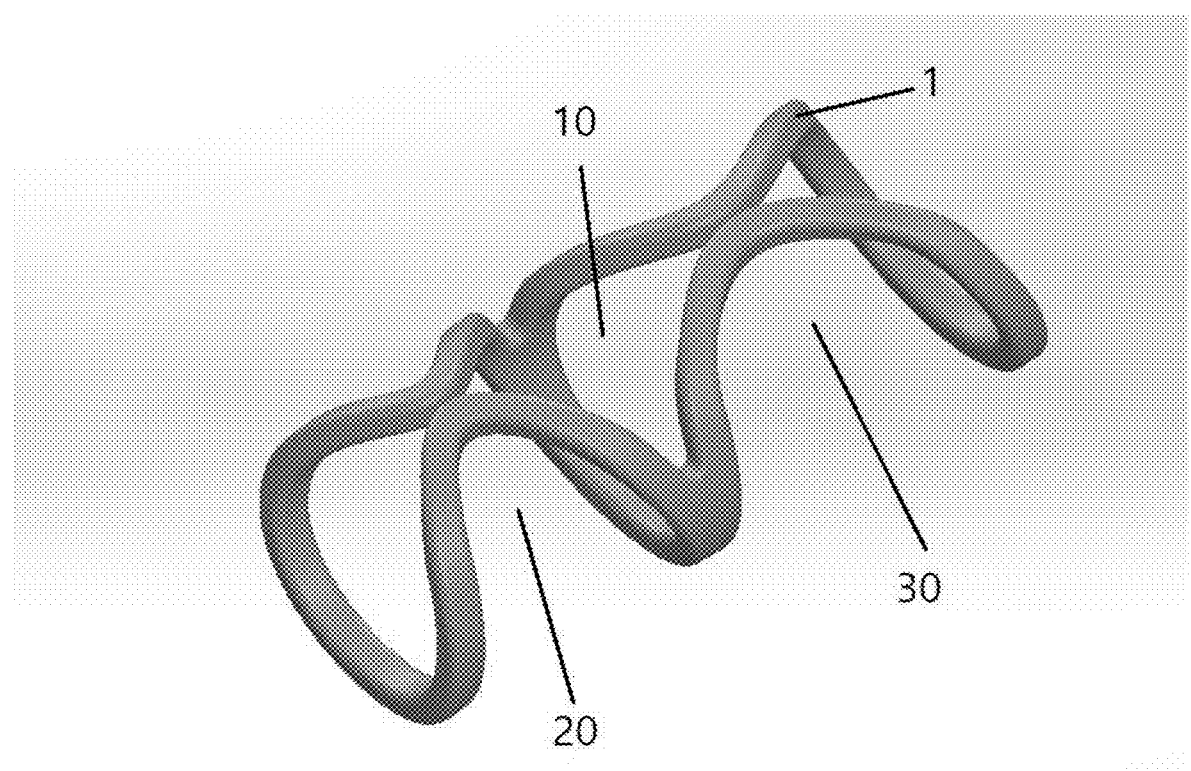
FIG. 1 is a perspective view illustrating an overall structure of a finger splint according to the present disclosure.

According to the best mode of the present disclosure, provided a finger splint for manual therapy, including: a base sheet including a metal material and having a predetermined length and width to surround a finger; a diamond-shaped base hole provided in a central portion of the base sheet; a first hole extending along the circumference of a portion of the finger to connect portions adjacent to right and left upper portions of the base hole; and a second hole extending along the circumference of the finger to connect portions adjacent to right and left lower portions of the base hole, with the position and size of the second hole corresponding to the position and size of the first hole.

MODE FOR INVENTION

Hereinafter, embodiments of the present disclosure will be described in detail with reference to the accompanying drawings. It should be understood that the accompanying drawings may not be drawn to scale, and the same or like reference numerals may be used to refer to the same or like elements throughout the drawings.

Figure 2:
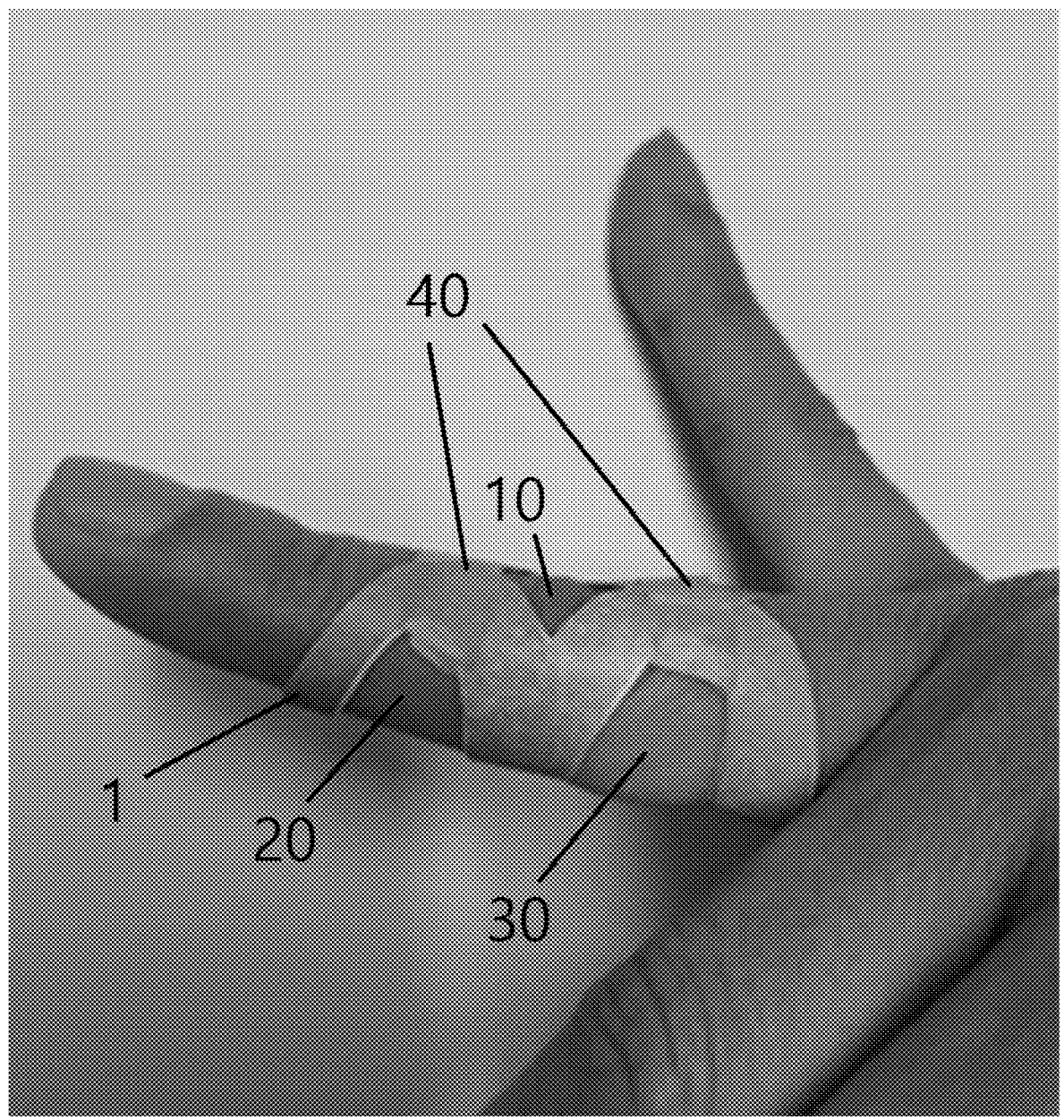
FIG. 2 is a schematic view illustrating the finger splint according to the present disclosure with respect to first and second holes, in which the finger splint is worn on a finger of a user.
Figure 3:
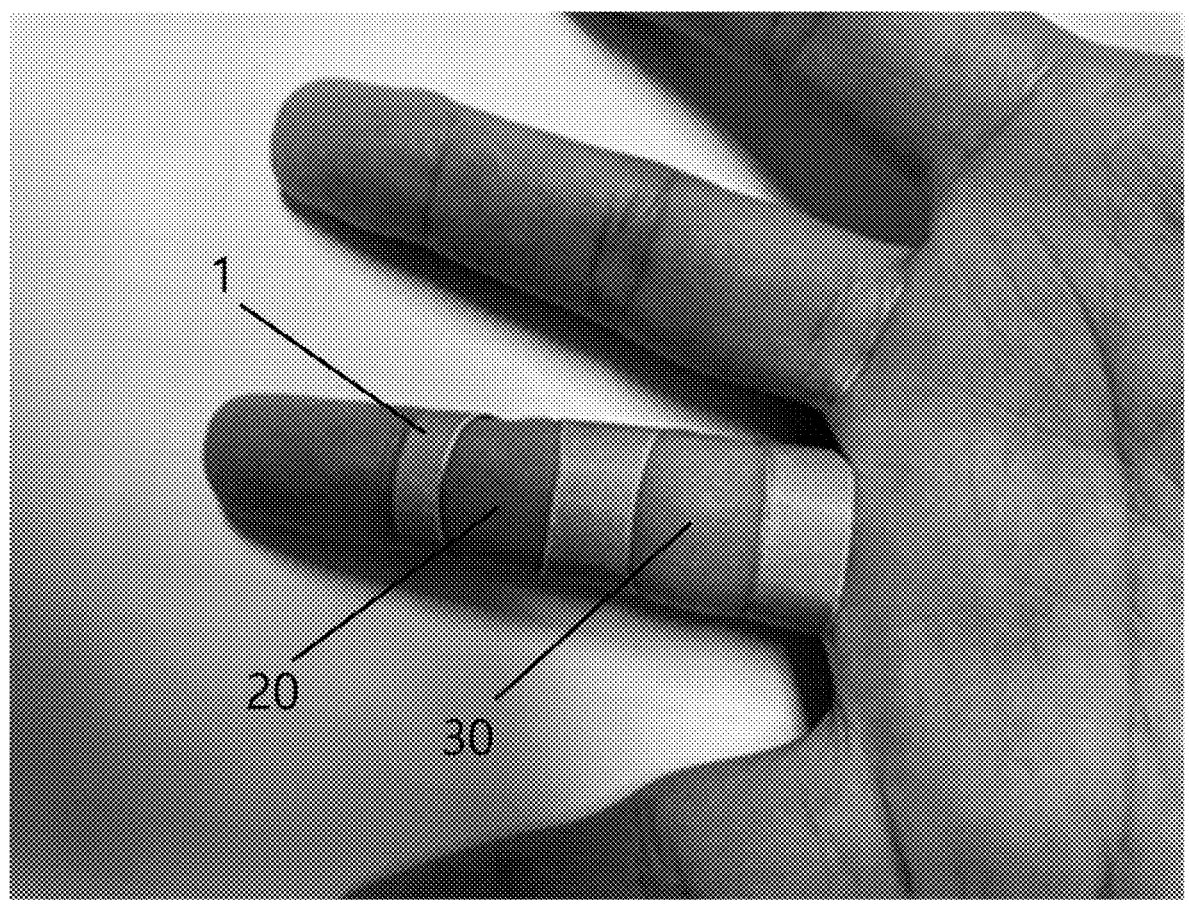
FIG. 3 is a schematic view illustrating the finger splint illustrated in FIG. 2 taken in the same direction as the palm of the user.

FIG. 1 is a perspective view illustrating an overall structure of a finger splint according to the present disclosure, FIG. 2 is a schematic view illustrating the finger splint according to the present disclosure with respect to first and second holes, the finger splint being worn on a finger of a user, and FIG. 3 is a schematic view illustrating the finger splint illustrated in FIG. 2 taken in the same direction as the palm of the user.

Figure 4:
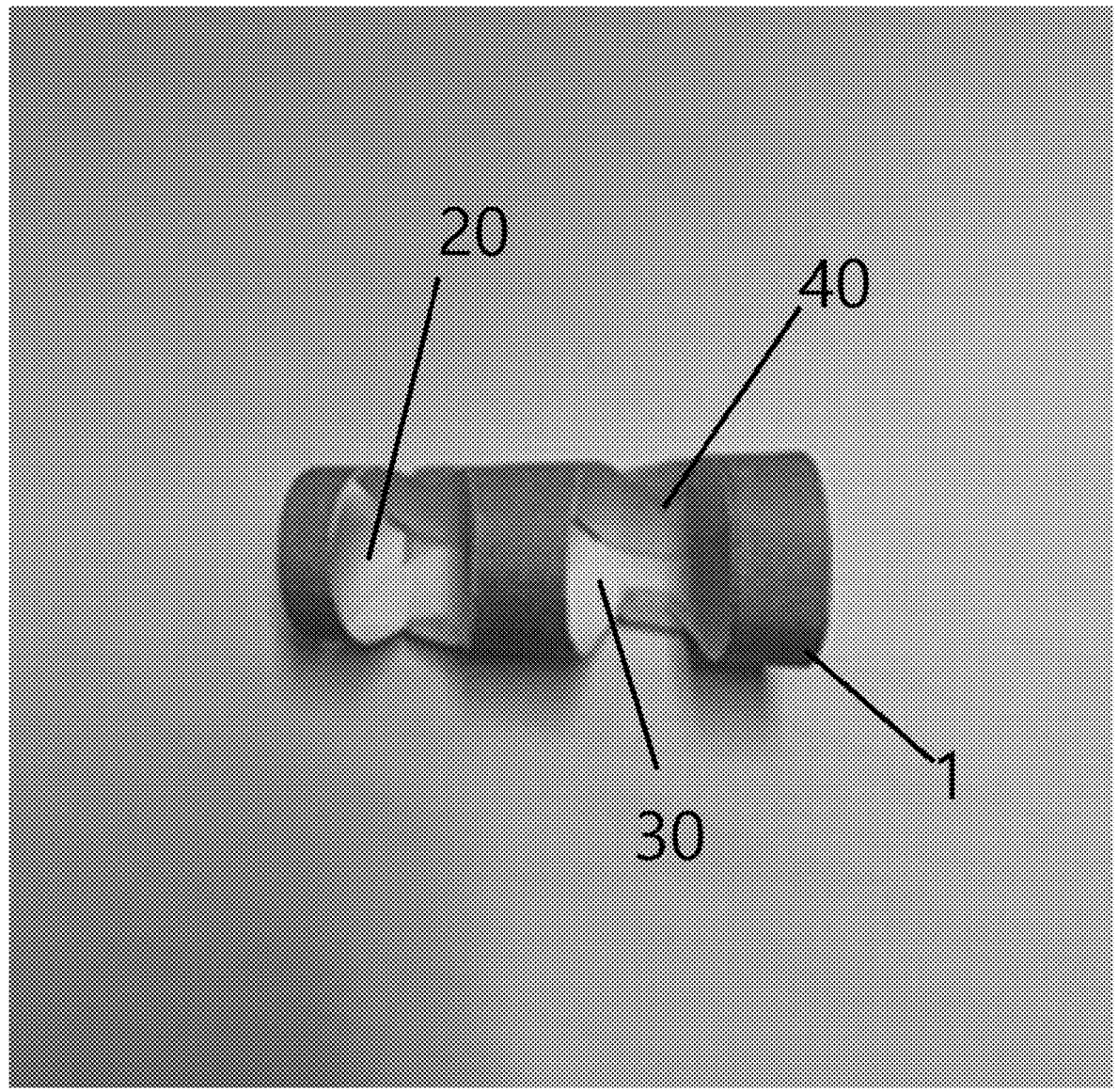
FIG. 4 is a schematic view illustrating the finger splint according to the present disclosure with respect to a base hole, in which the finger splint is removed from the finger of the user.
Figure 5:
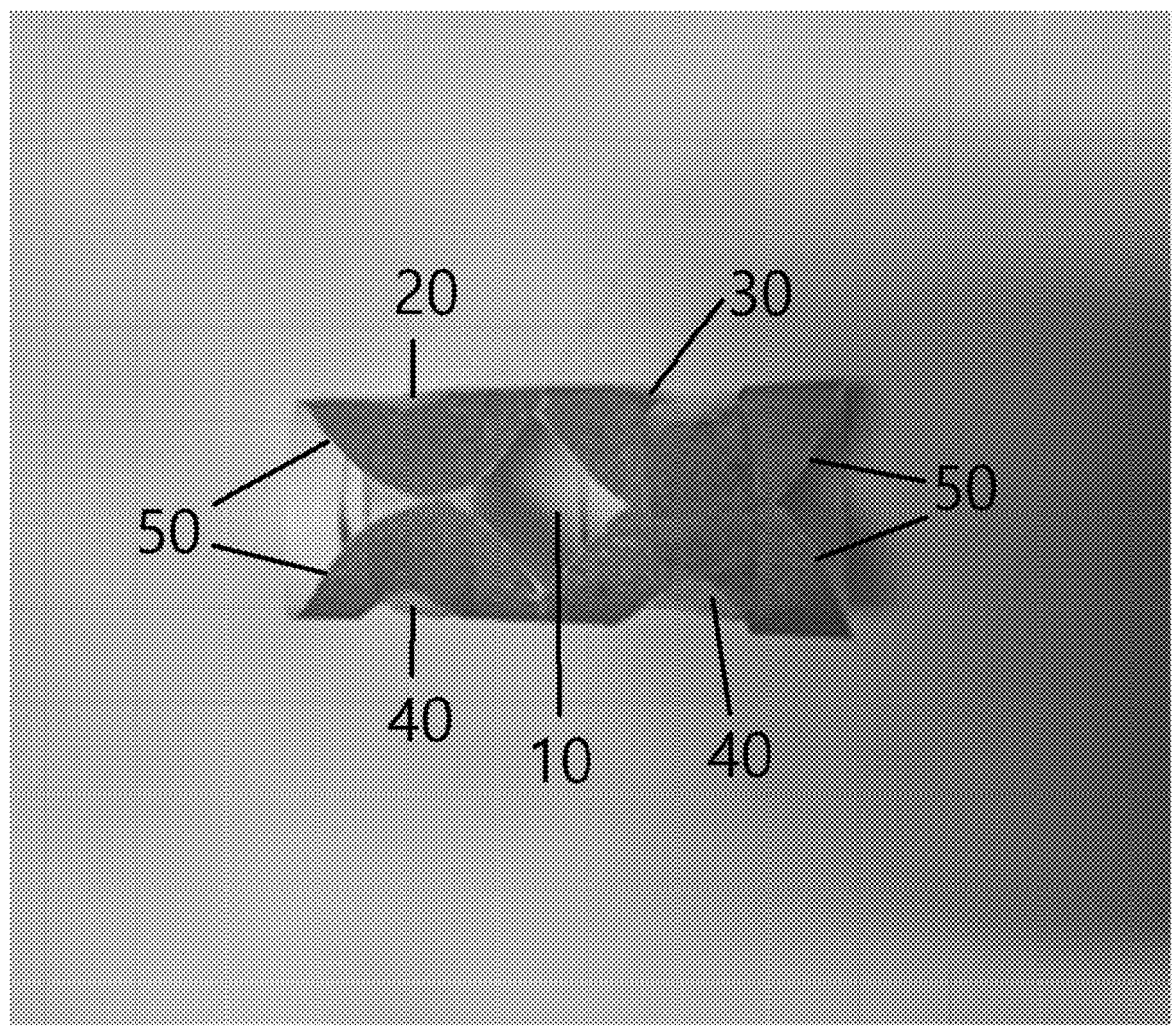
FIG. 5 is a rear view of FIG. 4.
Figure 6:
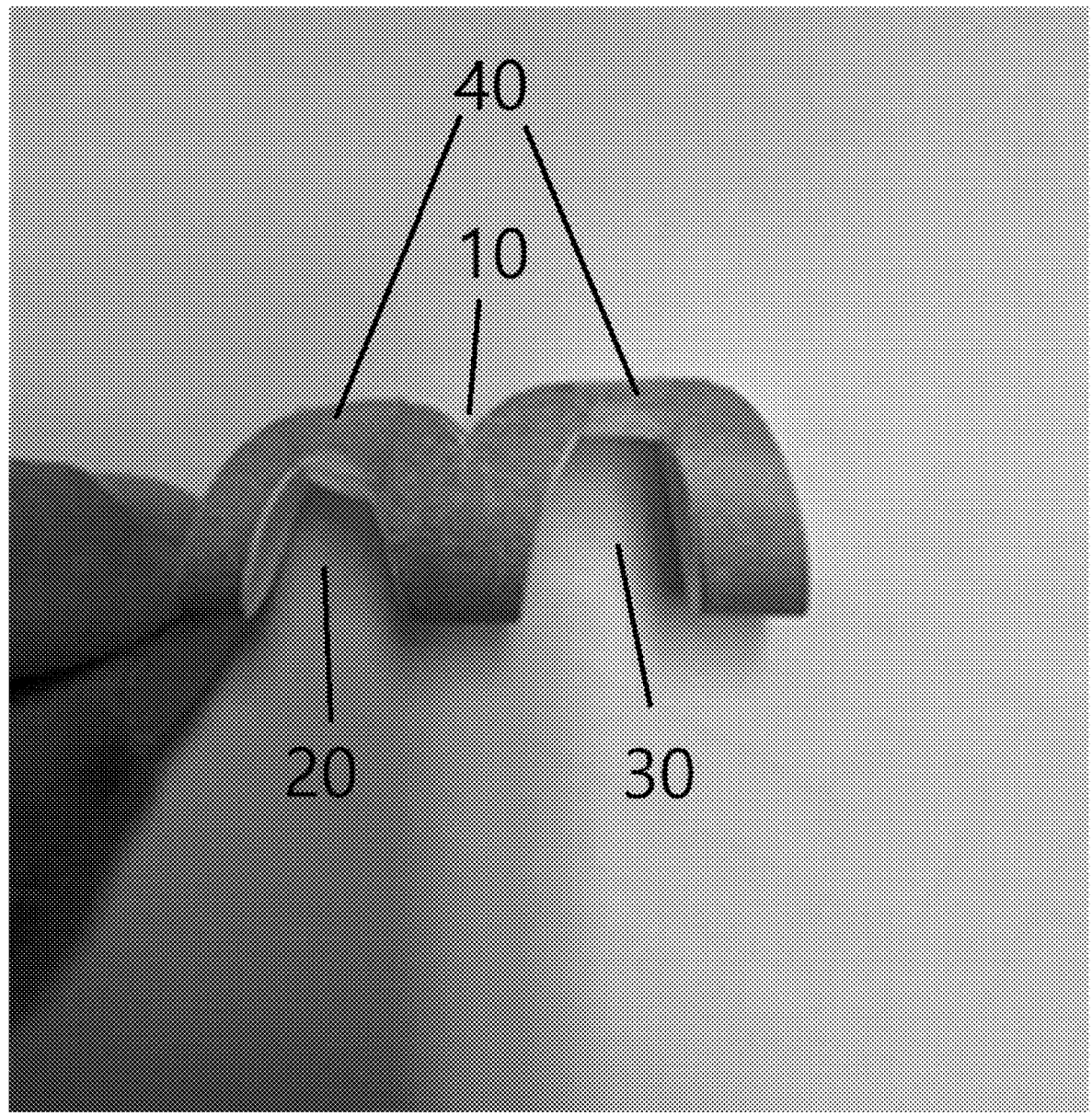
FIG. 6 is a schematic view illustrating the finger splint according to the present disclosure with respect to the first and second holes, in which the finger splint is removed from the finger of the user.

In addition, FIG. 4 is a schematic view illustrating the finger splint according to the present disclosure with respect to a base hole, the finger splint being removed from the finger of the user, FIG. 5 is a rear view of FIG. 4, and FIG. 6 is a schematic view illustrating the finger splint according to the present disclosure with respect to the first and second holes, the finger splint being removed from the finger of the user.

As can be seen from FIGS. 1 to 6, the finger splint according to the present disclosure is applied to a finger of a wearer such as a patient or a treatment target, and includes a base hole 10 and first and second holes 20 and 30 with respect to a base sheet 1.

The base sheet 1 has a size or volume capable of surrounding the finger. Specifically, the deployed shape (i.e., the deployment figure) of the base sheet 1 is a rectangular parallelepiped shape or a similar shape, with the height thereof corresponding to a predetermined height of the finger (e.g., the entire length of the finger or a shorter length), and the width thereof being equal to or greater than the circumferential length of the finger.

The base sheet 1 may be made of a metal material. That is, the base sheet 1 may not be easily torn by external impacts. At the same time, due to the unique flexibility of the metal, when the finger is bent or moved, the range of motion in which the base sheet may be bent or moved along with the finger may be advantageously obtained. In addition, the metal material is relatively hygienic and not harmful to the human body.

The metal material of the base sheet may be the same as of the material of the splint, which is made of a known metal material. For example, the metal material may be aluminum (Al). Thus, a description of specific metal materials will be omitted, since known technologies may be referred to for the metal material.

Although not shown in the drawings, connecting portions may be provided on both ends of the base sheet 1. The connecting portions may be connected to each other while winding along the circumference of the finger.

The connecting portions may have a variety of specific structures. For example, the base sheet 1 may be provided with a protrusion on one side thereof and a recess on both sides thereof, respectively, so as to be detachably connected to each other through engagement of the protrusion and the recess. Since each of the protrusion and the recess has the shape of a hook, the protrusion and the recess may be tightly fitted to each other to provide coupling force without loosening.

In addition, the connecting portions may be implemented as a magnetic coupling structure using magnets, or may have a plurality of fastening holes spaced apart predetermined distances and a plurality of fasteners, such as bolts, fitted into the fastening holes so as to adjust coupling positions or pressure according to setting of the coupling positions.

That is, the connecting portions for connecting both ends of the base sheet 1 may have a variety of known structures and means. Thus, the connecting portions according to the present disclosure are not limited to a specific structure.

Furthermore, typically, in each finger, the circumferential length of the outer end (i.e., the top end portion) is smaller than the circumferential length of the inner end (i.e., the bottom end portion). Accordingly, referring to FIGS. 4 to 6, the base sheet 1 may be configured to have a trapezoidal or similar profile shape when the base sheet 1 is wrapped (or rolled) around the finger. Here, when the base sheet 1 is spread or deployed, the deployed shape of the base sheet 1 is similar to the shape of an arc rather than that of a rectangular parallelepiped.

In this manner, it is possible to provide a feature capable of firmly wrapping the finger with the base sheet 1 while preventing the base sheet 1 having the rectangular parallelepiped deployed shape from becoming loose on the outer end of the finger or unnecessarily tightly fastened to the inner end of the finger.

The base hole 10 having the shape of a diamond is provided in the central portion or a portion close to the center of the base sheet 1.

As can be seen from FIGS. 1 to 6, when the finger splint according to the present disclosure is worn on the finger of the wearer, the base hole 10 is located in the same direction as the back of the hand, i.e., a side of the hand opposite the palm, instead of in the same direction as a side of the finger.

In the present disclosure, two through-holes are provided with respect to the base hole 10. The two through-holes will be referred to as the first hole 20 and the second hole 30.

With reference to FIG. 1, the first hole 20 is a hole extending in the circumferential direction of the finger to connect positions spaced apart predetermined distances from right and left peripheral portions of the top of the base hole 10 (i.e., the outer end of the finger). More specifically, the first hole 20 extends to connect the positions spaced apart predetermined distances from two upper sides (i.e., the right and left upper sides) of four sides of the diamond shape of the base hole 10.

In other words, the portion between both ends of the first hole 20 is located above the base hole 10. By as much as the portion between both ends of the first hole 20 is closed, the first hole 20 is opened along a portion of the circumference of the finger.

For example, in a state in which the center of the base hole 10 is set as the origin, when the longitudinal direction of the finger is referred to as the Y-axis and the circumferential direction of the finger perpendicular to the Y-axis is referred to as the X-axis, the second hole 30 is a hole formed in a portion of the base sheet 1 in which the first hole 20 is symmetrical about the X-axis.

That is, the second hole 30 may be a hole formed in the portions adjacent to the right and left sides of the bottom of the base hole 10 and along the circumference of the finger so as to match the position and size of the first hole 20.

Summarizing this structure, the base hole 10 having the diamond shape is formed in the central portion of the base sheet 1, and the first hole 20 and the second hole 30 have the same sizes. Here, the first hole 20 may be defined as a hole extending in the circumferential direction of the finger to connect positions perpendicularly spaced apart predetermined distances from the upper two sides, i.e., the upper right and left sides, of the base hole 10. The second hole 30 may be defined as a hole extending in the circumferential direction of the finger to connect positions perpendicularly spaced apart predetermined distances from the lower two sides, i.e., the lower right and left sides, of the base hole 10 so as to match the first hole 20.

According to this structure, the base hole 10 is formed in the same direction as the back of the hand, but the first and second holes 20 and 30 are formed in the same directions as the sides and the palm of the hand instead of in the same direction as the back of the hand.

The finger is bent toward the palm instead of toward the back of the hand. Thus, in the finger splint according to the present disclosure, the range of motion of the finger is obtained by providing the first and second holes 20 and 30 in the same direction as the palm, i.e., the line of motion in which the finger is bent, to be greater than the base hole 10. In this state, the base hole 10 is formed in the portion in the same direction as the back of the hand which is opposite the middle portion between the major portions of the first and second holes 20 and 30, thereby providing an excellent feature able to prevent the base sheet 1 from being moved or flexed along with the finger when the finger is moved.

Since the major objective of the finger splint according to the present disclosure is to fix the finger in the case of manual therapy, secondary objectives may be to primarily obtain the ability to fix the finger and secondarily prevent foreign body sensation and uncomfortableness by allowing the finger to move to a slight degree. According to the above-described structure, when the finger splint according to the present disclosure is worn on the finger, the finger may pivot in an operational (or pivot) angle range of 5 to 10°.

In summary, the finger splint according to the present disclosure may provide natural mobility to the finger so that the user does not feel inconvenient while firmly fixing the finger in the case of manual therapy. The finger splint may also have an ergonomic design by which the finger splint comfortably worn on the finger without becoming loose or applying uncomfortable pressure to the finger.

In addition, referring to FIGS. 1 and 2, a fixing band 40 may be detachably attached to the portion between the ends of the first hole 20 and the portion between the ends of the second hole 30.

The fixing band 40 is a band-shaped structure attached to the rear surface of the base sheet 1 which is supposed to be in contact with the finger. Particularly, the fixing band 40 is attached to the portions of the base sheet 1 between the ends of the first hole 20 and between the ends of the second hole 30 by means of an adhesive layer.

Here, the adhesive layer may be implemented using an adhesive component applied to an adhesive plaster well known in the art.

The fixing band 40 is respectively attached to the portions between the ends of the first hole 20 and between the ends of the second hole 30, in which the portions may be substantially in the opposite direction to the open areas defined by the first and second holes 20 and 30. Due to this configuration, the finger splint according to the present disclosure may reliably be in tight contact with the finger without being loosened when the finger is being moved while not interrupting the mobility of the finger enabled by the first and second holes 20 and 30. As a result, the finger splint may be provided with the finger fixing performance.

In addition, as can be seen from FIGS. 4 and 5, the fixing band 40 may be wrapped one time around the portion between the ends of the first hole 20 and the portion between the ends of the second hole 30.

That is, the portions between the ends of the first hole 20 and between the ends of the second hole 30 are also portions at which both ends of the base sheet 1 meet, and thus may be fixedly connected using the above-described connecting portions. Here, it is meant that the fixing band 40 may assist in fixedly connecting the both ends of the base sheet 1 while surrounding the portions between the ends in order to reinforce the function of the connecting portions.

Alternatively, none of the connecting portions may be provided, and the fixing band 40 may serve as the connecting portions.

In summary, the fixing band 40 is respectively attached to the portions between the ends of the first hole 20 and between the ends of the second hole 30 to provide a function of facilitating the finger splint being in close contact with the finger or surrounding the portions between the ends of the first hole 20 and between the ends of the second hole 30 to fixedly connect both ends of the base sheet 1

In addition, as can be seen from, for example, FIGS. 2 and 3, each of the first and second holes 20 and 30 may have an elliptical shape with the major axis thereof being in the circumferential direction of the finger.

In a case in which the first and second holes 20 and 30 are formed in the shape of rectangles having the same widths, when the finger is moved, repulsive force acts on the central portions of the first and second holes 20 and 30 in response to the movement of the finger. Thus, specific portions of the base sheet 10 adjacent to the first and second holes 20 and 30 may have increased fatigue or, in severe cases, cracks.

In order to overcome this problem, each of the first and second holes 20 and 30 may be ergonomically formed to have the elliptical shape, the major axis of which extends in the circumferential direction of the finger, instead of the rectangular shape. In particular, relatively greater repulsive force acting on the central portions than the lateral portions of the first and second holes 20 and 30 in response to the movement of the finger may be properly responded to, thereby preventing the above-described problems, i.e., cracks and inconvenient loosening, of the base sheet 1.

When each of the first and second holes 20 and 30 is formed in the elliptical shape as described above, four sides of the base hole 10 having the diamond shape do not linearly extend. Rather, as can be seen from FIG. 1, each of the four sides of the base hole 10 may extend in a shape convexly curved in the central direction of the base hole 10 to correspond to the elliptical shape of the first and second holes 20 and 30.

According to this structure, the portions between the first hole 20 and the base hole 10 and between the second hole 30 and the base hole 10 may have the same widths, thereby obtaining structural stability.

That is, when the base hole 10 maintains the diamond shape when the first and second holes 20 and 30 each having the elliptical shape are formed, it is possible to overcome the problems of non-uniform widths of the portions between the first hole 20 and the base hole 10 and between the second hole 30 and the base hole 10 and resultant increases in the degree of fatigue or the possibility of formation of cracks in specific portions.

Furthermore, rounded recesses 50 may be formed in at least some of the portions between the ends of the first hole 20 and between the ends of the second hole 30 that face the base hole 10 (i.e., the left portion in the case of the first hole and the right portion in the case of the second hole in FIG. 1). The rounded recesses 50 are indented in the direction of the base hole 10, and have shapes corresponding to the elliptical shapes of the first and second holes 20 and 30.

That is, when each of the first and second holes 20 and 30 has the elliptical shape, not only portions facing toward the base hole 10 but also outer portions facing away from the base hole 10 are rounded with the rounded recesses 50. Thus, not only the width between the first hole 20 and the outer portion (i.e., the left portion in FIG. 1) of the base sheet 1 but also the width between the second hole 30 and the opposite outer portion (i.e., the right portion in FIG. 1) may be processed to be the same. Consequently, structural durability may be obtained due to the above-described principle.

The base sheet 1 is made of the metal material as described above. The metal material having a high conductivity may sensitively react to the ambient temperature. Thus, the base sheet may deliver a sense of warm touch in the summer and a sense of cold touch in the winter. In this case, a foreign body sensation may be delivered to the wearer.

In addition, even in the case that the base sheet 1 has flexibility due to the unique properties of the metal material, the peripheral portions of the base sheet 1 may be formed sharp, thereby causing a problem in that the finger may be cut or pricked by an edge of the base sheet 1.

In order to prevent the foreign body sensation caused by the touch, provide a cushioning function, and directly provide a buffering function against the base sheet 1, a reinforcement layer may be stacked on the rear surface of the base sheet 1, i.e., a surface in contact with the finger. The reinforcement layer may include an elastic material such as silicone or rubber.

That is, the reinforcement layer provides a function able to minimize the problem that may occur when the base sheet 1 made of the metal material as described above is in direct contact with the skin.

Furthermore, the reinforcement layer may also include a functionality component in addition to the elastic material.

Specifically, the reinforcement layer may include 90 to 99 weight parts of an elastic material such as silicone or rubber and 1 to 10 weight parts of a reinforcement material including alkyl acrylate which is one of methyl acrylate, ethyl acrylate, and propyl acrylate.

Alkyl acrylate is one of methyl acrylate, ethyl acrylate, and propyl acrylate. Such alkyl acrylate is water repellent, and thus may additionally provide a water repellent function when added as a composition of the reinforcement layer. Such alkyl acrylate is also adhesive, and thus may provide the reinforcement layer with an effect able to further improve anti-slip performance, i.e., non-slip performance.

Thus, as the reinforcement material including alkyl acrylate is added, the reinforcement layer in direct contact with the finger, i.e., the skin, may become water repellent so as not to be contaminated with sweat or the like released from the skin. Non-slip performance of the reinforcement layer may also be improved so as to more effectively prevent the reinforcement layer from being released from the finger.

In addition, such a reinforcement material may further include an additional composition in addition to above-described alkyl acrylate, thereby further enhancing the function of the reinforcement layer.

Specifically, the reinforcement material may be manufactured by a process including a first solution manufacturing step S11, a second solution manufacturing step S12, and a reinforcement material completing step S13.

(S11) First Solution Manufacturing Step

First, a first solution is manufactured by mixing 15 to 25 weight parts of alkyl acrylate, 20 to 30 weight parts of ethylene vinyl acetate (EVA), and 45 to 60 weight parts of toluene.

As described above, alkyl acrylate is a water repellent and adhesive material, and toluene is added as a solvent of the first solution.

In addition, ethylene vinyl acetate (EVA) added together with alkyl acrylate is a material produced by polymerizing two monomers, i.e., a copolymer of ethylene monomer and vinyl acetate (VA) monomer. Ethylene vinyl acetate has excellent shock absorption ability at low temperatures due to the flexibility thereof, has good weather resistance, tear strength, stress crack resistance, and ozone resistance, and excellent bonding ability and processability. Thus, in response to the addition of the ethylene vinyl acetate, the weather resistance, tear strength, stress crack resistance, and ozone resistance may be improved and the adhesion may also be improved, thereby improving non-slip performance.

(S12) Second Solution Manufacturing Step S12

Afterwards, the second solution is manufactured by mixing 75 to 85 weight parts of the first solution, 15 to 20 weight parts of polyvinylidene fluoride, 5 to 10 weight parts of phosphite ester (or phosphorous acid ester) and 3 to 10 weight parts of benzotriazole.

Polyvinylidene fluoride is a thermoplastic fluoropolymer having excellent chemical resistance and a high melting point of 171° C. Polyvinylidene fluoride is a material having excellent mechanical properties unlike other fluoropolymers. Polyvinylidene fluoride also has excellent chemical resistance, impact resistance, and the like. Thus, in response to the addition of such polyvinylidene fluoride, not only the chemical resistance of the reinforcement material but also the chemical resistance of the reinforcement layer may be improved.

Phosphite ester is an ester of phosphorous acid, and is added to serve as an antioxidant in order to prevent the reinforcement layer including the elastic material from being oxidized by moisture, in particular, sweat, through contact with the skin and the quality of the reinforcement layer from being impaired.

Benzotriazole is a colorless granular compound having a needle-shaped crystal structure. Benzotriazole may be added to provide a function of a UV stabilizer. Such benzotriazole may reduce or delay the penetration of ultraviolet (UV) radiation, thereby assisting in preventing the reinforcement layer from being exposed to UV radiation by which the reinforcement layer would be oxidized and the quality thereof would be impaired.

(S13) Reinforcement Material Completing Step S13

Finally, the reinforcement material is completed by mixing 85 to 95 weight parts of the second solution, 5 to 10 weight parts of polybutylene adipate-co-terephthalate, and 1 to 10 weight parts of a discoloration inhibitor including zinc oxide.

Polybutylene adipate-co-terephthalate is an eco-friendly polymer material harmless to the human body, and has eco-friendly and high-strength properties. When added to the reinforcement material, polybutylene adipate-co-terephthalate serves to improve the physical properties and strength of the reinforcement layer including the reinforcement material.

In addition, the discoloration inhibitor is characterized by including zinc oxide as an active ingredient. Such zinc oxide may improve structural stability, durability, and heat resistance. Moreover, zinc oxide may serve to prevent, for example, coloration, material deformation, and malfunction of the reinforcement layer which is a surface in contact with the skin, thereby assisting in preserving the functional stability of the reinforcement layer.

In summary, as the reinforcement material having the above-described specific composition and manufactured by the above-described process is added to the reinforcement layer, it is possible to prevent contamination or malfunction caused by sweat released from the human body by improving water repellency. It is also possible to improve non-slip performance by improving adhesion. Thus, it is possible to prevent the finger splint from being unnecessarily released from the finger to be pressed or fixed. High strength and chemical resistance may be expected. Furthermore, it is possible to prevent the reinforcement material from being discolored even in the case that the reinforcement material is repeatedly used or is exposed to sweat.

The configuration and operation of the finger splint for manual therapy according to the present disclosure have been described with reference to the drawings. It should be understood, however, that the foregoing descriptions are illustrative only, the technical idea of the present disclosure is not limited to the foregoing descriptions or the accompanying drawings, and various modifications and changes in forms are possible without departing from technical idea of the present disclosure.

INDUSTRIAL APPLICABILITY

The finger splint for manual therapy according to the present disclosure can be sold in orthopedic hospitals, pharmacies, or various places allowed to sell therapeutic products, and can also be manufactured by mass production. Therefore, the present disclosure is regarded as having high industrial applicability.

The invention claimed is:

1. A finger splint for manual therapy, comprising:
a base sheet comprising a metal material and having a predetermined length and width configured to surround a finger;
a diamond-shaped base hole provided in a central portion of the base sheet;
a first hole configured to extend along a circumference of a first portion of the finger to connect portions adjacent to right and left upper portions of the base hole; and
a second hole configured to extend along the circumference of a second portion of the finger to connect portions adjacent to right and left lower portions of the base hole, with the position and size of the second hole corresponding to the position and size of the first hole,
wherein the base sheet comprises:
a first ring-shaped portion comprising the first hole; and
a second ring-shaped portion disposed in contact with the first ring-shaped portion and comprising the second hole, and
wherein an end and an opposite end of the first ring-shaped portion are connected by a first connecting portion and an end and an opposite end of the second ring-shaped portion are connected by a second connecting portion such that the first ring-shaped portion and the second ring-shaped portion are configured to surround an entire circumference of the finger when viewed from a tip of the finger.

2. The finger splint of claim 1, wherein the base sheet is configured to have a trapezoidal profile shape when configured to wrap around the finger.

3. The finger splint of claim 1, wherein the first and second connecting portions comprise a fixing band comprising an adhesive layer on a rear surface thereof.

4. The finger splint of claim 1, wherein each of the first and second holes has an elliptical shape with a major axis thereof being in a circumferential direction of the finger.

5. The finger splint of claim 4, wherein four sides of the base hole are convexly rounded and extend toward a center of the base hole to correspond to the elliptical shapes of the first and second holes.

6. The finger splint of claim 4, wherein rounded recesses are provided in at least some of the first and second connecting portions between ends of the first hole and between ends of the second hole that face the base hole, are indented in a direction of the base hole, and have shapes corresponding to the elliptical shapes of the first and second holes.

7. The finger splint of claim 1, wherein a reinforcement layer comprising an elastic material is attached to a surface of the base sheet configured to contact with the finger.

8. The finger splint of claim 7, wherein the reinforcement layer comprises:
90 to 99 weight parts of the elastic material; and 1 to 10 weight parts of a reinforcement material comprising alkyl acrylate which is one of methyl acrylate, ethyl acrylate, and propyl acrylate.

9. The finger splint of claim 8, wherein the reinforcement material is manufactured by steps of:
   manufacturing a first solution by mixing 15 to 25 weight parts of the alkyl acrylate, 20 to 30 weight parts of ethylene vinyl acetate (EVA), and 45 to 60 weight parts of toluene;
   manufacturing a second solution by mixing 75 to 85 weight parts of the first solution, 15 to 20 weight parts of polyvinylidene fluoride, 5 to 10 weight parts of phosphite ester, and 3 to 10 weight parts of benzotriazole; and
   completing the reinforcement material by mixing 85 to 95 weight parts of the second solution, 5 to 10 weight parts of polybutylene adipate-co-terephthalate, and 1 to 10 weight parts of a discoloration inhibitor comprising zinc oxide.

* * * * *